(12) United States Patent
Fedick

(10) Patent No.: US 11,635,353 B2
(45) Date of Patent: Apr. 25, 2023

(54) SAMPLE COLLECTION DEVICE

(71) Applicant: The United States of America, as represented by the Secretary of the Navy, Arlington, VA (US)

(72) Inventor: Patrick W. Fedick, Ridgecrest, CA (US)

(73) Assignee: The United States of America, as represented by the Secretary of the Navy, Washington, DC (US)

( * ) Notice: Subject to any disclaimer, the term of this patent is extended or adjusted under 35 U.S.C. 154(b) by 168 days.

(21) Appl. No.: 16/903,647

(22) Filed: Jun. 17, 2020

(65) Prior Publication Data

US 2021/0396627 A1    Dec. 23, 2021

(51) Int. Cl.
*G01N 1/08* (2006.01)
*G01N 33/24* (2006.01)

(52) U.S. Cl.
CPC .............. *G01N 1/08* (2013.01); *G01N 33/24* (2013.01); *G01N 2223/616* (2013.01)

(58) Field of Classification Search
CPC ..... G01N 1/08; G01N 33/24; G01N 2223/616
See application file for complete search history.

(56) References Cited

U.S. PATENT DOCUMENTS

| | | | | |
|---|---|---|---|---|
| 2,321,639 A * | 6/1943 | Zarbo | ................... | B01D 29/085 141/331 |
| 2,456,912 A * | 12/1948 | Burrows | ................ | B01D 35/28 229/4.5 |
| 2,633,410 A * | 3/1953 | Beckley | ............. | G01N 33/6827 422/534 |
| 2,671,715 A * | 3/1954 | Beckley | ................. | G01N 33/68 422/534 |
| 5,051,584 A * | 9/1991 | Gray | ..................... | H01J 49/105 250/281 |
| 5,078,189 A * | 1/1992 | Ronsonet | ................ | B67C 11/02 141/331 |
| 5,480,072 A * | 1/1996 | Ripley | .................... | B67C 11/02 141/334 |
| 5,793,039 A * | 8/1998 | Oishi | .................... | H01J 49/067 250/288 |
| 6,803,568 B2 * | 10/2004 | Bousse | ............... | H01J 49/0018 250/281 |
| 8,460,782 B2 * | 6/2013 | Ivanov | .................... | C04B 35/16 428/297.4 |
| 9,346,045 B2 * | 5/2016 | Blumentritt | ............. | G01F 23/02 |
| 10,545,073 B2 * | 1/2020 | Pawliszyn | ................ | G01N 1/36 |
| 10,559,455 B2 * | 2/2020 | Cooks | ................. | H01J 49/0409 |
| 10,578,579 B2 * | 3/2020 | Alonso Chamarro | . | G01N 33/24 |
| 2007/0084996 A1 * | 4/2007 | Li | ......................... | H01J 49/167 250/282 |

(Continued)

FOREIGN PATENT DOCUMENTS

| | | | | |
|---|---|---|---|---|
| CN | 104392886 A * | 3/2015 | ............. | G01N 27/62 |
| EP | 762473 A2 * | 3/1997 | ......... | G01N 30/7266 |

*Primary Examiner* — John Fitzgerald
(74) *Attorney, Agent, or Firm* — Naval Air Warfare Center Weapons Division; Matthew D. Pangallo; Stuart H. Nissim

(57) ABSTRACT

A sample collection device is composed of a conductive polymer. The conductive polymer includes a mixture of carbon nanotubes and a polymer. The sample collection device has a hole at a tip of the sample collection device with the hole having a size ranging from about 0.15 mm to about 0.25 mm.

20 Claims, 13 Drawing Sheets

(56) References Cited

U.S. PATENT DOCUMENTS

| | | | |
|---|---|---|---|
| 2011/0009774 A1* | 1/2011 | Calasso | A61B 5/15151 |
| | | | 600/583 |
| 2011/0263005 A1* | 10/2011 | Chang | C12M 35/02 |
| | | | 435/283.1 |
| 2013/0136672 A1* | 5/2013 | Blumentritt | G01F 23/02 |
| | | | 422/524 |
| 2013/0181010 A1* | 7/2013 | Ouyang | H01J 49/0027 |
| | | | 222/209 |
| 2014/0001415 A1* | 1/2014 | Sheng | H01B 1/04 |
| | | | 264/105 |
| 2014/0241956 A1* | 8/2014 | Page | G01N 1/14 |
| | | | 422/534 |
| 2017/0053788 A1* | 2/2017 | Cha | H01J 49/167 |
| 2017/0071710 A1* | 3/2017 | Deturmeny | A61C 17/02 |
| 2017/0105707 A1* | 4/2017 | Senior | A61B 10/0038 |
| 2017/0322179 A1* | 11/2017 | Alonso Chamarro | |
| | | | G01N 27/4035 |

* cited by examiner

SAMPLE COLLECTION DEVICE

STATEMENT REGARDING FEDERALLY SPONSORED RESEARCH OR DEVELOPMENT

The invention described herein may be manufactured and used by or for the government of the United States of America for governmental purposes without the payment of any royalties thereon or therefor.

BACKGROUND

Soil or solid media sample analyses are performed for many reasons, which include determining concentrations of plant nutrients, fertilizer concentrations, the composition of an unknown substance, and the presence of contaminants in a sample. Generally, testing solid media includes sample extraction from the source being tested, transportation to the laboratory, chromatographic separation, and mass spectrometry detection. Other chromatography methods and ambient ionization techniques may be used. Ambient ionization methods have become the standard practice because these methods may not require a chromatographic separation step and may also utilize portable mass spectrometry devices to eliminate inefficiencies in solid media analysis.

BRIEF DESCRIPTION OF THE DRAWINGS

Features and advantages of examples of the present disclosure will be apparent by reference to the following detailed description and drawings, in which like reference numerals correspond to similar, though perhaps not identical, components. Reference numerals or features having a previously described function may or may not be described in connection with other drawings in which they appear.

DETAILED DESCRIPTION

Figure 1:
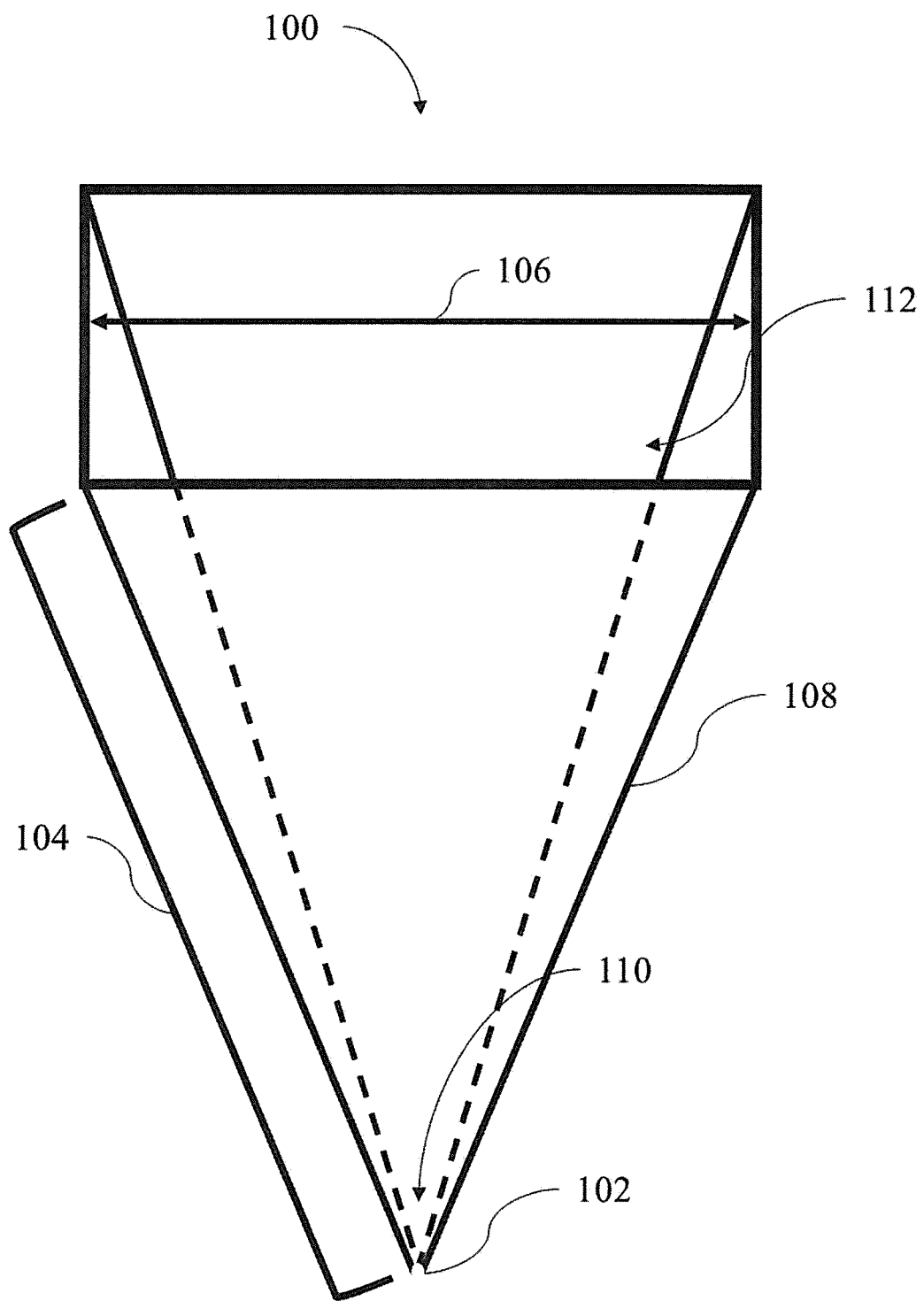
FIG. 1 is an isometric view of an example of the sample collection device described herein.

Paper cone spray ionization (PCSI) uses a three-dimensional variant of paper spray ionization. PCSI employs a hydrophobic wax paper cone as the sample holder, extraction chamber, and disposable ionization source. Solid media (e.g., bulk soil, sediments, solid waste, etc.) containing the analyte can be placed into the wax paper pyramidal structure, in which an in-situ solid-liquid extraction occurs after solvent addition. The sample is analyzed using Paper Cone Spray Ionization Mass Spectrometry (PCSI MS). PCSI is a promising in-situ analysis due to its simplicity and minimalistic preparation requirements. In addition, PCSI sources are inexpensive and couple well to portable mass spectrometers, which can increase the efficiency of PCSI methods.

Despite the emerging benefits of PCSI, there are still many drawbacks to the PCSI materials and methods. Regarding the materials, PCSI uses hydrophobic wax paper cones as the sample holder, extraction chamber, and disposable ionization source. The wax paper material has a thickness of about 180 μm, which makes these wax paper cones less durable. Therefore, the paper cones are more prone to irreparable damage, especially while using them in the field. Additionally, the paper cones are disposable, one-time use cones. Therefore, they have to be reproduced for each sample and disposed of after the sample analysis.

Regarding the PCSI methods, the paper cones are handmade and therefore lack consistency in size and shape due to human error. As a result, there is a lack of reproducibility when making paper cones, and therefore, more inconsistency in the methods used. Additionally, the PCSI method requires training to make the paper cones consistently and operate a mass spectrometer. Therefore, this method can accumulate expenses from the cost to train individuals to properly produce the paper cones and operate a mass spectrometer.

First, in the invention herein, the sample collection device is composed of a conductive polymer, which includes a polymer and carbon nanotubes with a thickness of at least 600 μm or greater. The material is thicker, much more durable, and therefore, significantly less likely to have irreparable damage. Additionally, in some examples, the sample collection device herein can be cleaned and reused after analyzing a sample without returning to the laboratory. Therefore, less devices are needed to collect and run an analysis on solid media when compared to the wax paper cones.

Furthermore, the ionization method using the sample collection device herein is more efficient compared to a traditional PCSI method. The sample collection device herein improves the testing reproducibility because the collection devices may be produced using a 3D printer. Additionally, the sample collection device requires minimal training due, in part, to the sample collection device being 3D printed and reusable rather than handmade and disposable. Furthermore, sample analysis using this sample collection device is more efficient compared to PCSI using paper cones because the sample collection devices are identical, therefore less time is spent positioning the cone in front of the mass inlet to run a sample using the mass spectrometer.

The invention herein includes a sample collection device composed of a conductive polymer. The conductive polymer includes a mixture of carbon nanotubes and a polymer. The sample collection device has a hole at a tip on the sample collection with the hole having a size ranging from about 0.15 mm to about 0.25 mm. The sample collection device can be used to collect solid media containing an analyte, applying a solvent and a voltage to the sample collection device, and performing a sample analysis.

Referring now to FIG. 1, an isometric view of an example of the sample collection device 100 is shown. The sample collection device 100 includes a hole 102 at the tip 110 of the sample collection device. The sample collection device 100 also includes a hollow interior 112 that forms a cavity, which can hold a solid media sample. The sample collection device 100 can be any hollow shape that terminates at a point and that can hold a solid media sample while allowing solvent extraction from the device during ambient ionization for mass spectrometer analysis. For example, the sample collection device may be a hollow multifaced pyramid or a hollow cylindrical cone.

The hole 102 at the tip 110 allows for solvent extraction after the solvent has passed through the solid media during ambient ionization. The hole 102 is an opening or open space at one end of the sample collection device 100. In an example, the opening, or open space, is formed at a point or tip 110 at one end of the sample collection device 100. The hole 102 must have a diameter that is small enough to retain the solid media sample, but large enough to allow the solvent to exit the device for analysis in a mass spectrometer. In an example, the hole has a diameter ranging from about 0.15 mm to about 0.25 mm.

The sample collection device 100 is composed of a conductive polymer, which is not shown in FIG. 1. The sample collection device 100 shown in FIG. 1 is for illustrative purposes only and should not be construed as being limiting or directed to a particular material or materials. The conductive polymer includes a polymer and carbon nanotubes. The polymer may be any polymer that can be subjected to a voltage and is immiscible with the extraction and spray solvent. For example, the polymer may be polyethylene terephthalate, acrylonitrile butadiene styrene, polylactic acid, polyetherketoneketone, polyether ether ketone, polycarbonate, polyphenylene sulfide, polyvinylidene fluoride, and combinations thereof. The carbon nanotubes may be any carbon nanotubes that conduct electricity. An example of the carbon nanotubes is multi-wall carbon nanotubes.

Referring back to FIG. 1, the sample collection device 100 also has a height 104 and a width 106. The height 104 and width 106 can be any height and width that is large enough to hold a solid media sample, but small enough to remain portable while using the least amount of material as possible. The height is defined as the distance from the hole 102 at the tip 110 of the sample collection device 100 to the base of the sample collection device 100. The width 106 is defined as the furthest distance from the inner side of a wall to the opposite inner side of a wall of the sample collection device 100. In an example, the sample collection device may have a height 104 and a width 106 ranging from about 12.5 mm to about 40 mm.

Referring to FIG. 1, the sample collection device 100 also has a thickness 108. The thickness 108 of the sample collection device 100 must be large enough to hold a solid media sample, but small enough to retain the device's original shape while using the least amount of material as possible. The thickness 108 is defined as the distance from the inner side of a wall to the outer side of a wall. In an example, the sample collection device 100 has a thickness 108 ranging from about 0.6 mm to about 3 mm.

The sample collection device 100 can be made using any known methods to produce a conductive polymer device. In an example, the sample collection device 100 is produced using a 3D printer and a conductive polymer capable of being 3D printed. In an example, a MakerGear M2 3D printer was used with 3DXSTAT®ESD PETG as the conductive polymer. Once the sample collection device 100 is produced using 3D printing, it may be used immediately to collect samples for mass spectrometer analysis.

The invention herein also includes a method for examining solid media composition. The method includes preparing the sample collection device, filling the sample collections with solid media containing an analyte, applying a solvent to the solid media and applying a voltage to the sample collection device, and performing a sample analysis, thereby determining an analyte composition, analyte concentration, or analyte presence within the solid media.

Figure 2:
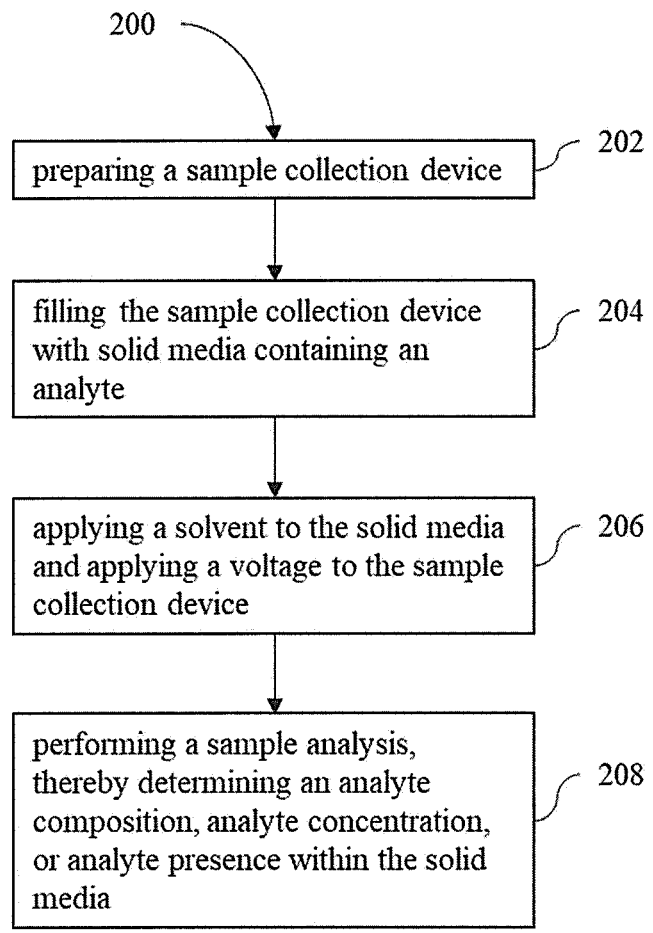
FIG. 2 is a flow diagram illustrating an example of a method for examining solid media composition described herein.
Figure 3A:
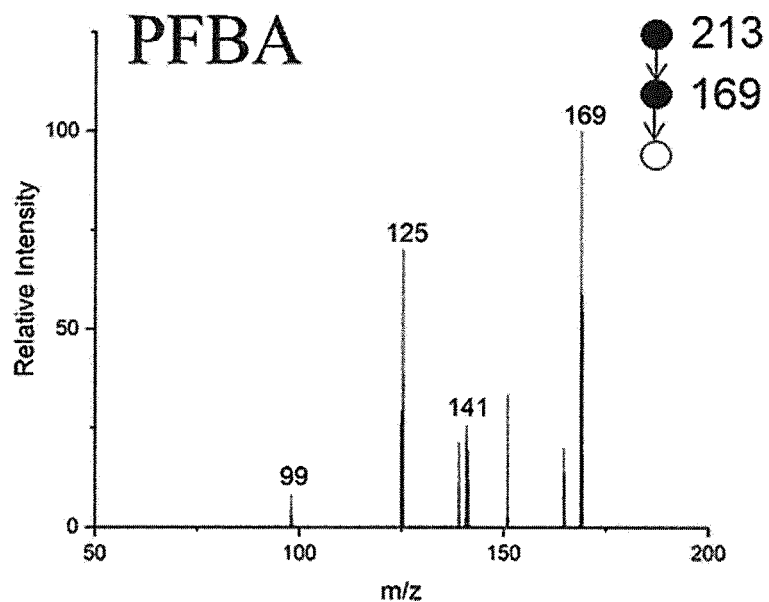
FIG. 3A-FIG. 3K are eleven MS3 mass spectra of the mass to charge ratio (X-axis, labeled "m/z") vs. the relative intensity (Y-axis, labeled "relative intensity") for eleven per and polyfluoroalkyl substances mixed in soil.
Figure 3B:
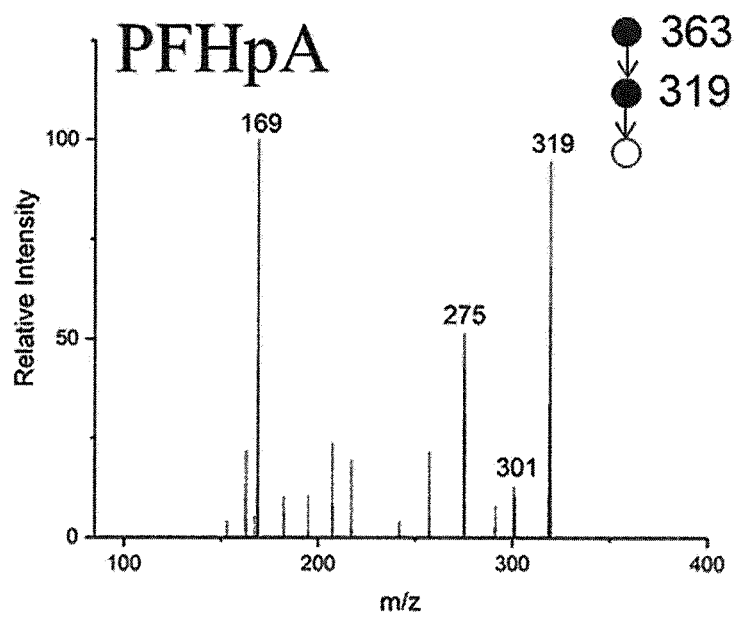
Figure 3C:
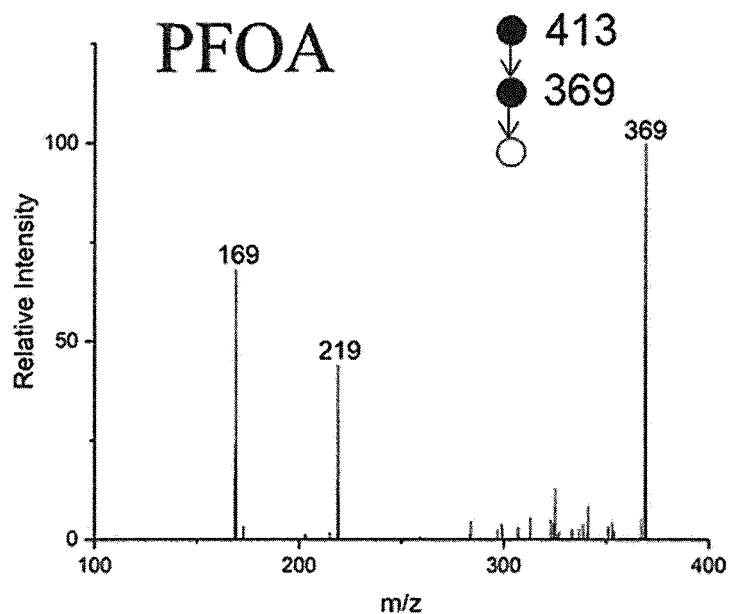
Figure 3D:
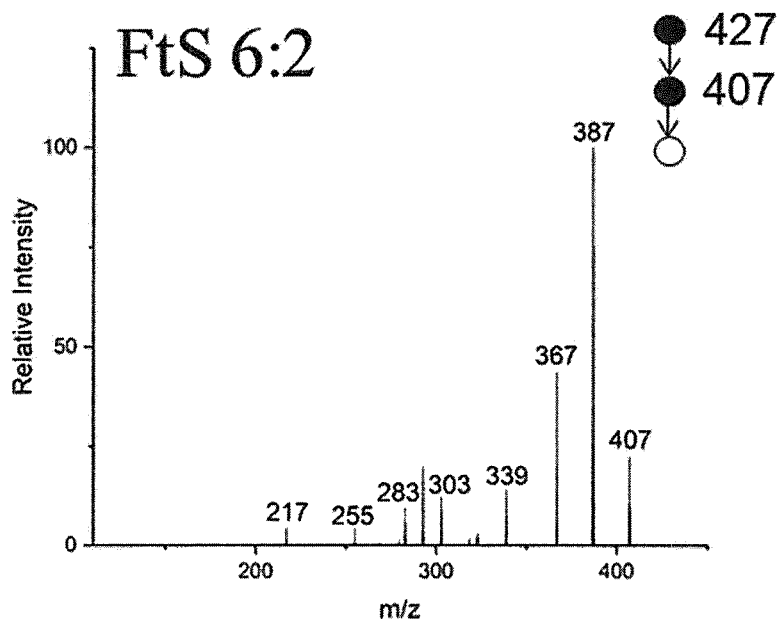
Figure 3E:
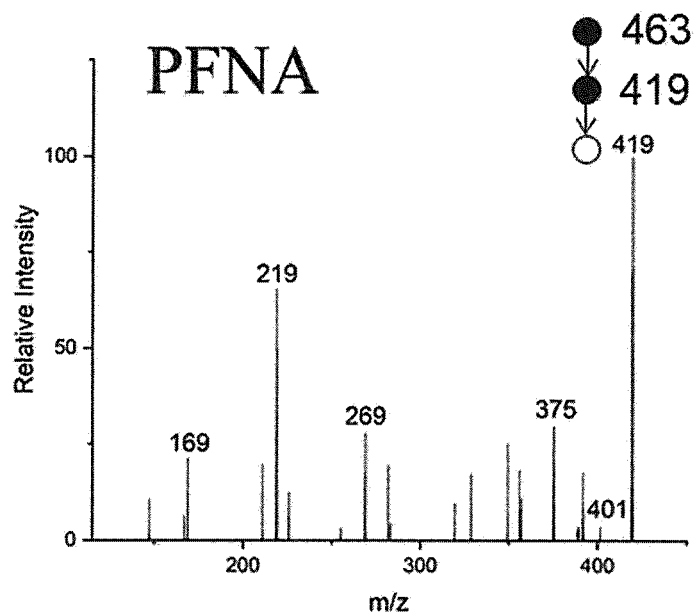
Figure 3F:
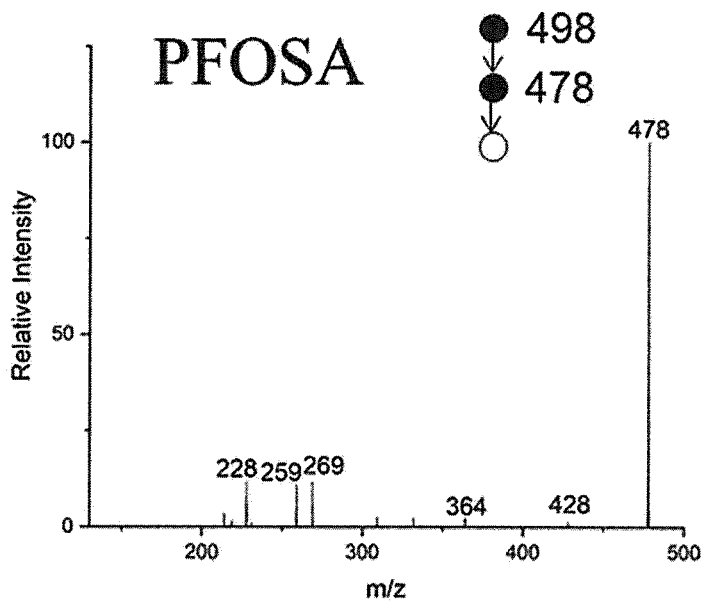
Figure 3G:
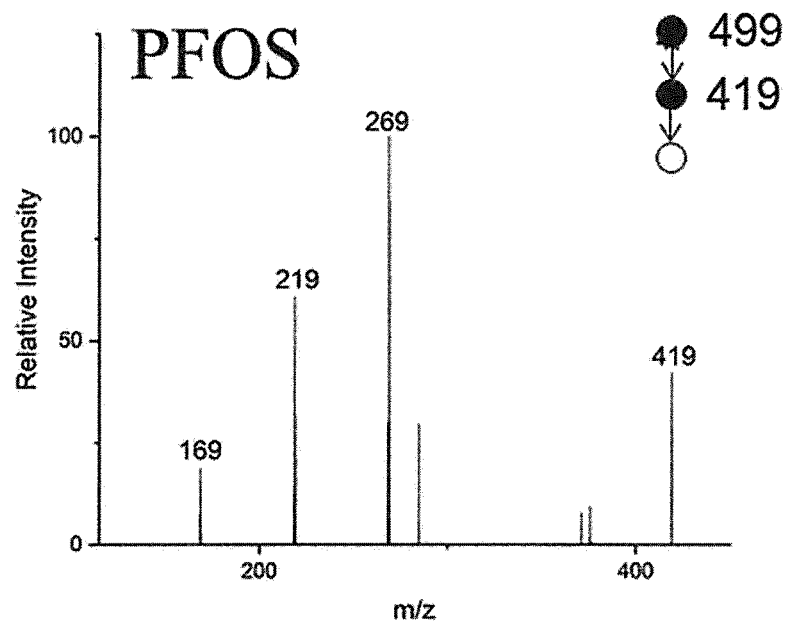
Figure 3H:
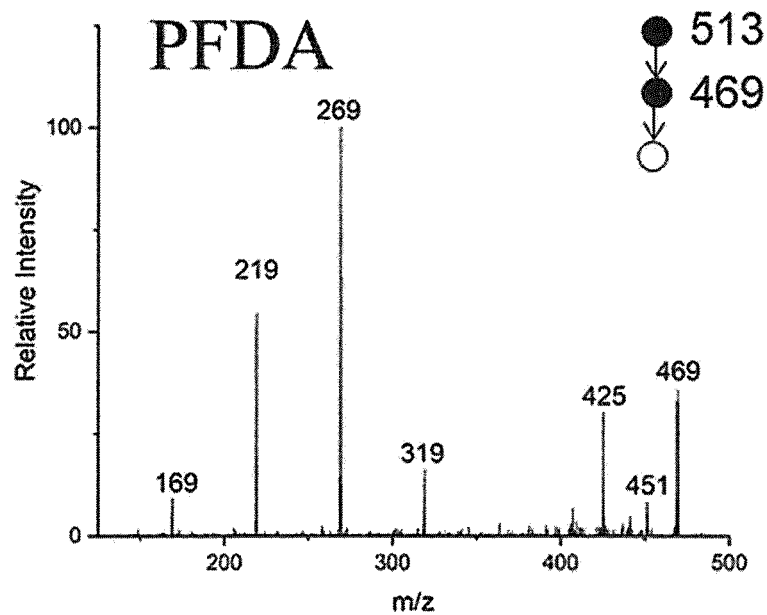
Figure 3I:
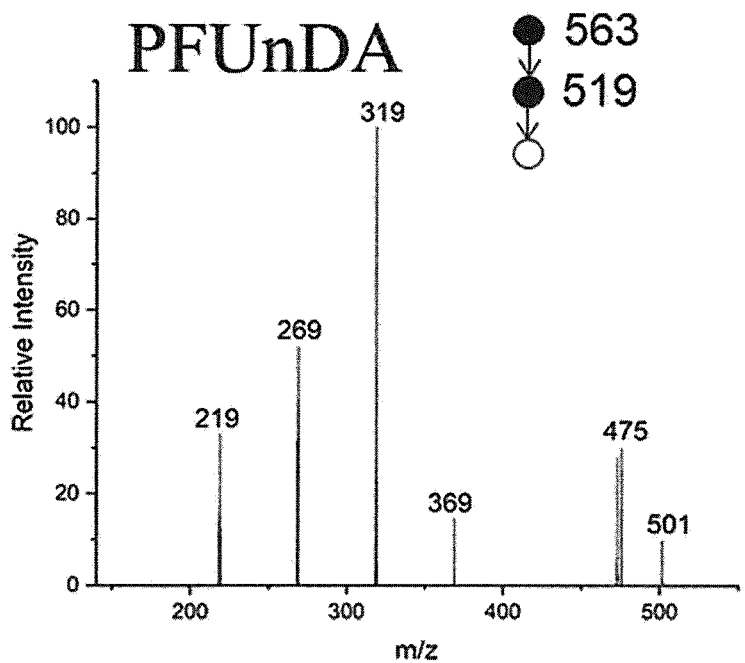
Figure 3J:
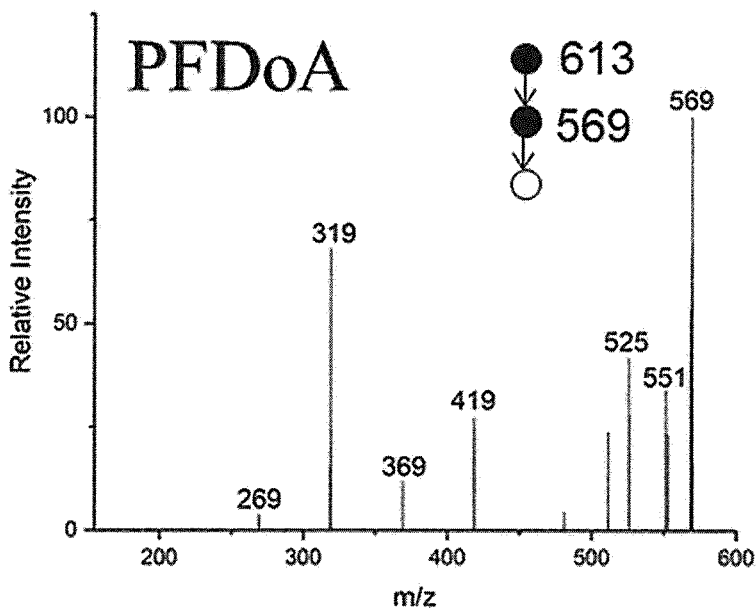
Figure 3K:
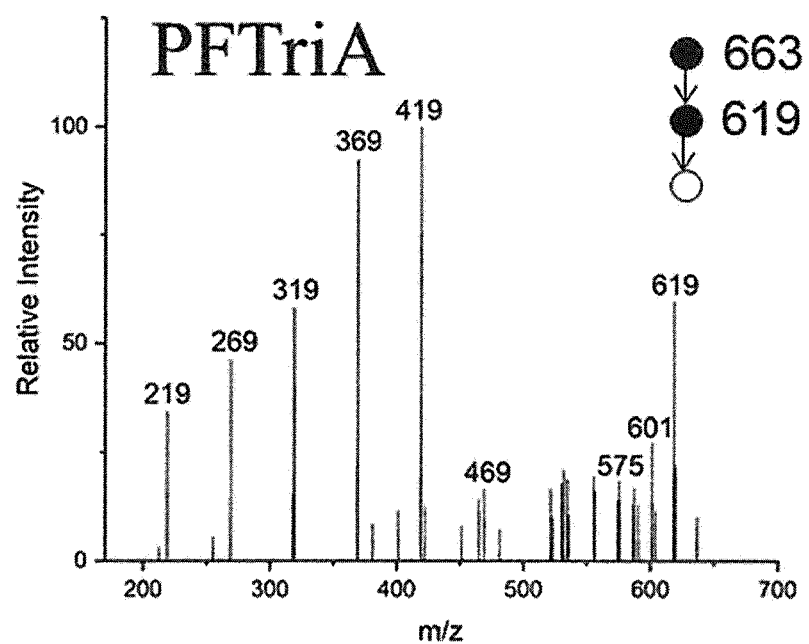
Figure 4A:
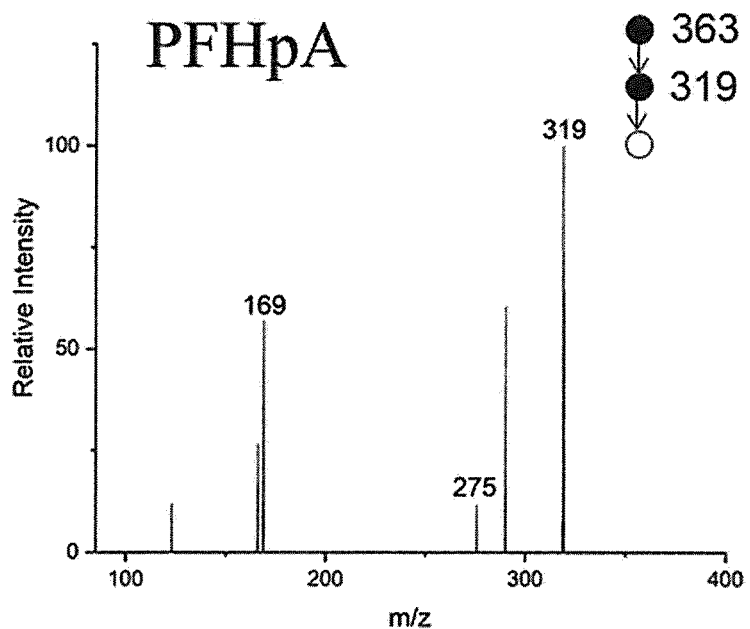
FIG. 4A-FIG. 4H are eight $MS^3$ mass spectra of the mass to charge ratio (X-axis, labeled "m/z") vs. the relative intensity (Y-axis, labeled "relative intensity") for eight per and polyfluoroalkyl substances found in a 3M AFFF sample mixed in soil.
Figure 4B:
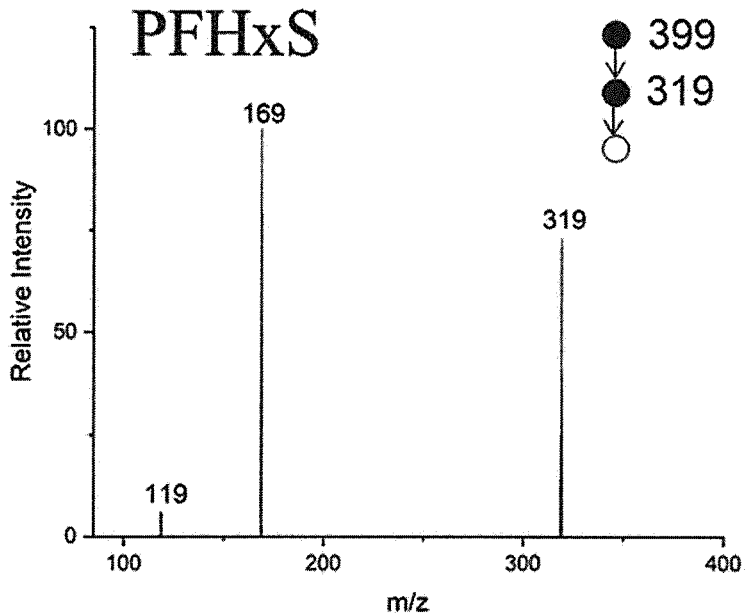
Figure 4C:
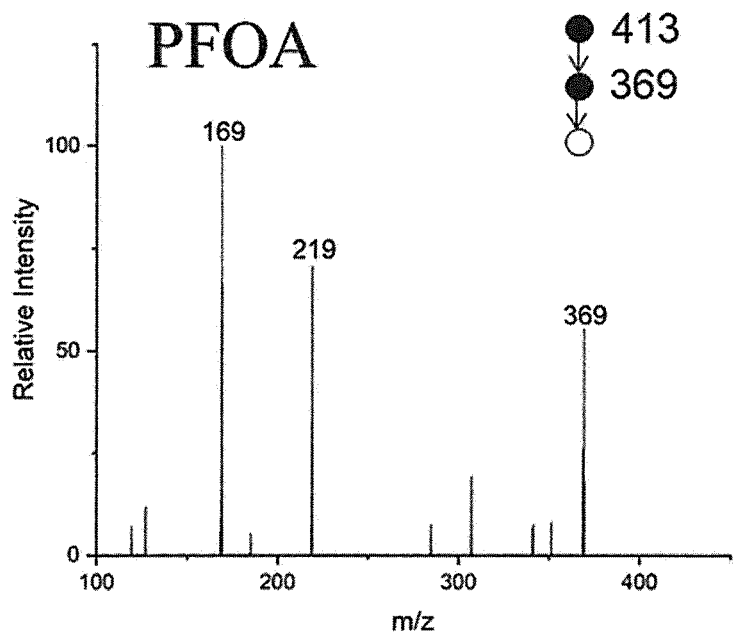
Figure 4D:
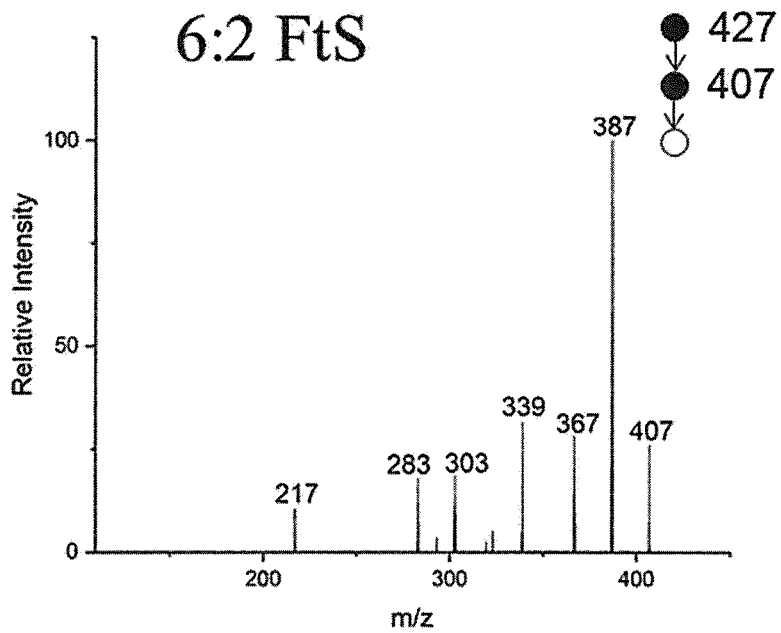
Figure 4E:
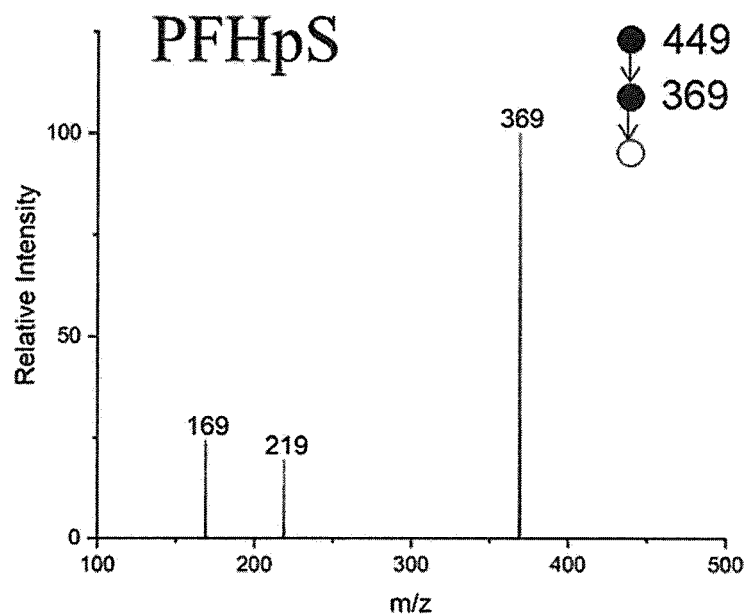
Figure 4F:
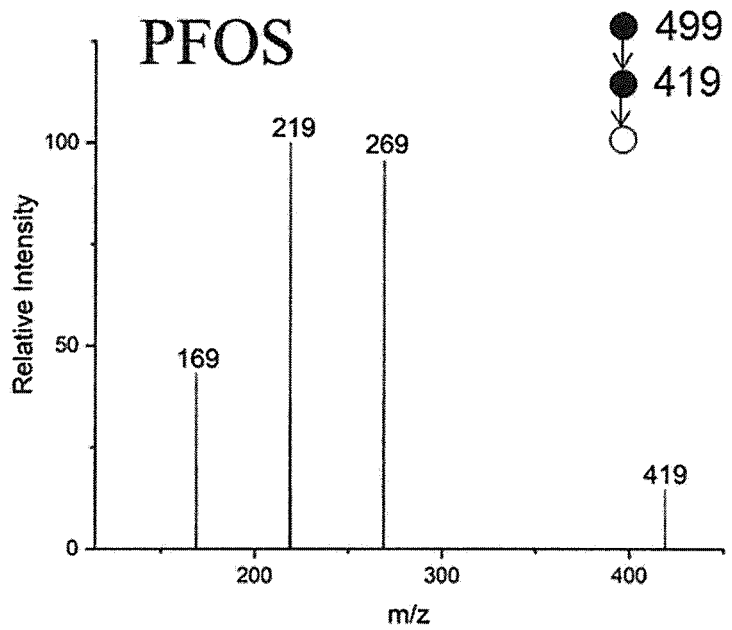
Figure 4G:
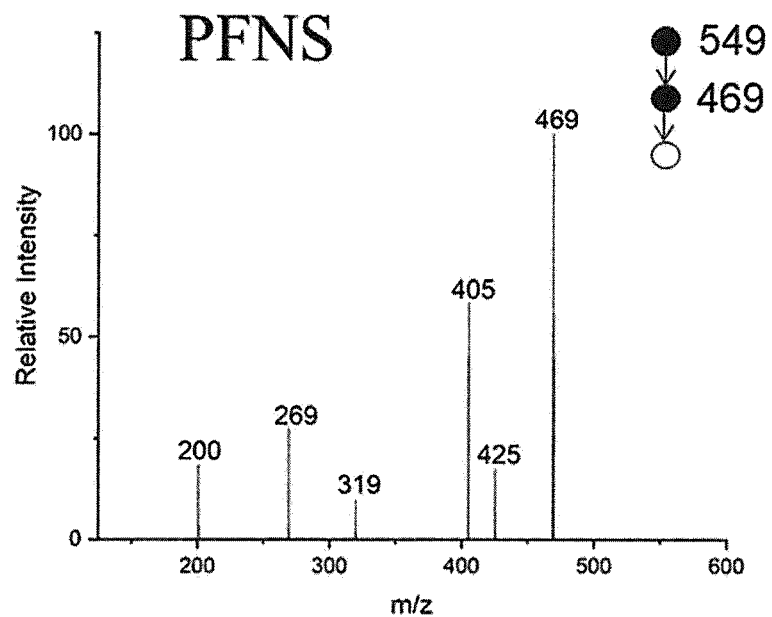
Figure 4H:
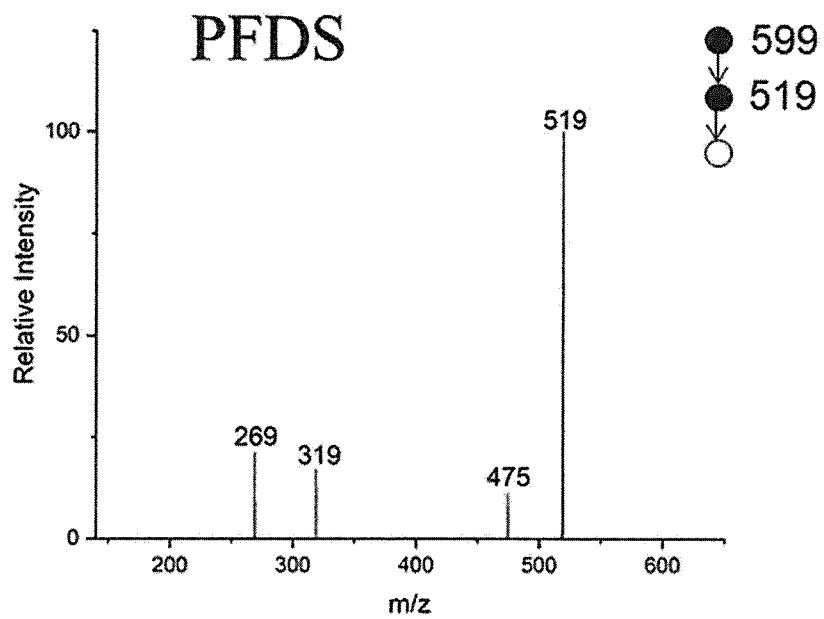

Referring to FIG. 2, the method 200 includes step 202 of preparing the sample collection device 100. The sample collection device 100 is the same sample collection device previously mentioned herein. The sample collection device 100 may also be prepared as previously described herein. In some examples, the sample collection device 100 may be cleaned and reused in the field or at the laboratory to obtain another solid media sample. In other examples, the sample collection device 100 is discarded after sample collection. In an example, when the sample collection device 100 is cleaned and reused, the solid media is removed from sample collection device 100 and the sample collection device 100 is submerged and sonicated in a solvent. The submerging and sonication step is repeated until the sample collection device 100 is cleaned (i.e., a clean standard sample is run with the sample collection device 100, which shows no chemicals present). In some examples, different solvents are used to clean the sample collection device 100 each time the sample collection device 100 is submerged and sonicated.

Referring back to FIG. 2, step 204 of method 200 includes filling the sample collections with solid media containing an analyte. In some examples, the sample collection device 200 is taken to an area containing solid media that needs to be evaluated. In other examples, the solid media is brought to a laboratory where the sample collection device 200 can be used to evaluate the solid media sample. Some examples of the solid media may be soil, sand, sediment, waste, pure analytes, and combinations thereof.

The analytes may a number of different substances. Some examples of analytes include perfluoroalkyl substances, polyfluoroalkyl substances, energetics, chemical warfare agent simulant, drugs of abuse, pesticides, and combinations thereof. Any perfluoroalkyl substances, polyfluoroalkyl substances, energetics, chemical warfare agent simulant, drugs of abuse, or pesticides known to those skilled in the art may be used as the analyte depending on the purpose of evaluating the solid media. Some specific examples of perfluoroalkyl substances include perfluorodecanoic acid, heptafluorobutyric acid, perfluorotridecanoic acid, perfluoroheptanoic acid, perfluorooctane-sulfonic acid, Perfluoroundecanoic acid, perfluorooctance-sulfonamide, tridecafluorooctane-1-sulphonic acid, perfluorooctanoic acid, perfluorononanoic acid, tricosafluorododecanoic acid, or combinations thereof.

Referring to FIG. 2, step 206 of the method 200 includes applying a solvent and a voltage to the solid media in the sample collection device 100. In this step 206, the solvent extracts the analyte and separates the analyte from the solid media to the solvent within the sample. The voltage is applied to the sample collection device 100 to form a spray plume at the tip 110 where the hole 102 is located in the sample collection device 100. The analyte is ionized and analyzed. In an example, the voltage ranges from about 4 kV to about 7 kV and may be applied for a time ranging from about to about.

The solvent extracts the analyte within the solid media sample. Some examples of the solvent include methanol, ethanol, propanol, isopropanol, acetonitrile, water, water mixed with organic solvents, and combinations thereof. The amount of solvent varies depending on the size of the sample collection device 100 and the solid matrix. The amount solvent is directly proportional to the size of the sample collection device (i.e., as the size of the sample collection device increases, so does the amount of solvent that is required). Similarly, in another example, to increase the amount of time a spray plume is being produced, more solvent may be added. In any example, the solvent may be added sequentially (e.g., three 2 mL aliquots) or all at once (e.g., one 6 mL portion). In an example, the solvent is added in aliquots ranging from about 1 mL to about 2 mL.

In some examples, an additive is used in conjunction with the solvent. The additive assists with the extraction of the analyte of the solid media. The additive is added to the solvent prior to adding the solvent to the solid media within the sample collection device to form a mixture of the solvent and additive. Some examples of the additive that may be used with the solvent include acetic acid, formic acid, ammonium acetate, and combinations thereof. The amount of additive differs based on the additive and solvent that is used. For example, a mixture of methanol as the solvent and 1% formic acid as the additive may be used.

Referring to FIG. 2, step 208 of the method 200 includes performing a sample analysis, thereby determining an analyte composition, analyte concentration, or analyte presence within the solid media. The analyte composition, analyte concentration, or analyte presence is determined by analyte standards of the molecule of interest. For example, if the data from the sample matches the standard, the target analyte is present. The analysis may be performed by any known mass spectrometer or an ion mobility spectrometer by loading the solvent with the analyte into the spectrometer. The mass spectrometer or ion mobility spectrometer may be a portable or a benchtop spectrometer. The mass spectrometer or ion mobility spectrometer performs the analysis using any known techniques.

The method 200 may be repeated for each sample that needs to be examined. For mass spectrometry, about 60 samples can be examined in the same time as one sample is examined for liquid chromatography mass spectrometry (LC-MS). The data is presented as a plot of the intensity vs. the mass-to-charge ratio that can provide the analyte presence, analyte concentration, and, in some instances, the analyte composition.

To further illustrate the present disclosure, examples are given herein. It is to be understood that these examples are provided for illustrative purposes and are not to be construed as limiting the scope of the present disclosure.

EXAMPLES

Example 1: Preparing a Sample Collection Device

A MakerGear M2 3D printer was used to construct the sampling and ionization cones. The printer utilized conductive ESD-Safe PETG 3D printing filament that was constructed with multi-wall carbon nanotube to permit conductivity. The cones were designed using Autodesk Inventor and converted to an STL file and sliced using Simplify3D. The glass printing platform was prepared with Kapton Tape and heated to 80° C. A 0.35 mm stainless steel extruder nozzle was utilized and was held at 250° C. for the entire print. The square pyramidal cones had a length of 30 mm, a width of 30 mm and a height of 29.3 mm. The hole at the apex of the cone was about 0.2 mm.

Example 2: Lab Generated Soil Samples

A 10 ppb mixture of eleven per and polyfluoroalkyl substance (PFAS) standards was dispensed onto about 1 g of soil, mixed, and allowed to dry. The sample collection device described in Example 1 was then used to collect mass spectra of the eleven PFAS standards using 3D-PCSI-MS. The $MS^3$ spectra of eleven PFAS were identified in top soil. The eleven PFAS demonstrated are perfluorobutanoic acid (PFBA), perfluoroheptanoic acid (PFHpA), perfluorooctanoic acid (PFOA), fluorotelomer sulfonic acid 6:2 (FtS 6:2), perfluorononanoic acid (PFNA), perfluorooctanesulfonamide (PFOSA), perfluorooctanesulfonic acid (PFOS), perfluorodecanoic acid (PFDA), perfluoroundecanoic acid (PFUnDA), perfluorododecanoic acid (PFDoA), and perfluorotridecanoic acid (PFTriA). FIG. 3A-3K show the eleven mass spectra with each spectrum labeling the PFAS found in the soil sample.

Example 3: Lab Generated AFFF Soil Samples

A 3M aqueous film forming foam (AFFF) sample was diluted and deposited onto a soil sample. The AFFF sample was prepared by performing a 1000× dilution of the concentrate and dispensing 100 µL onto about 1 g of soil, mixed, and allowed to dry. The sample collection device described in Example 1 was then used to collect mass spectra of the AFFF sample using 3D-PCSI-MS. The $MS^3$ spectra of eight PFAS were identified in the soil sample. The eight PFAS identified included perfluoroheptanoic acid (PFHpA) (363 m/z), perfluorohexanesulphonic acid (PFHxS) (399 m/z), perfluorooctanoic acid (PFOA) (413 m/z), fluorotelomer sulfonic acid 6:2 (6:2 FtS) (427 m/z), perfluoroheptanesulfonic acid (PFHpS) (449 m/z), perfluorooctanesulfonic acid (PFOS) (499 m/z), perfluorononanesulfonic acid (PFNS) (549 m/z), and perfluorodecanesulfonic acid (PFDS) (599 m/z). FIG. 4A-FIG. 4H show the eight mass spectra with each spectrum labeling the PFAS found in the soil sample.

Example 4: Field Test Samples

Figure 5:
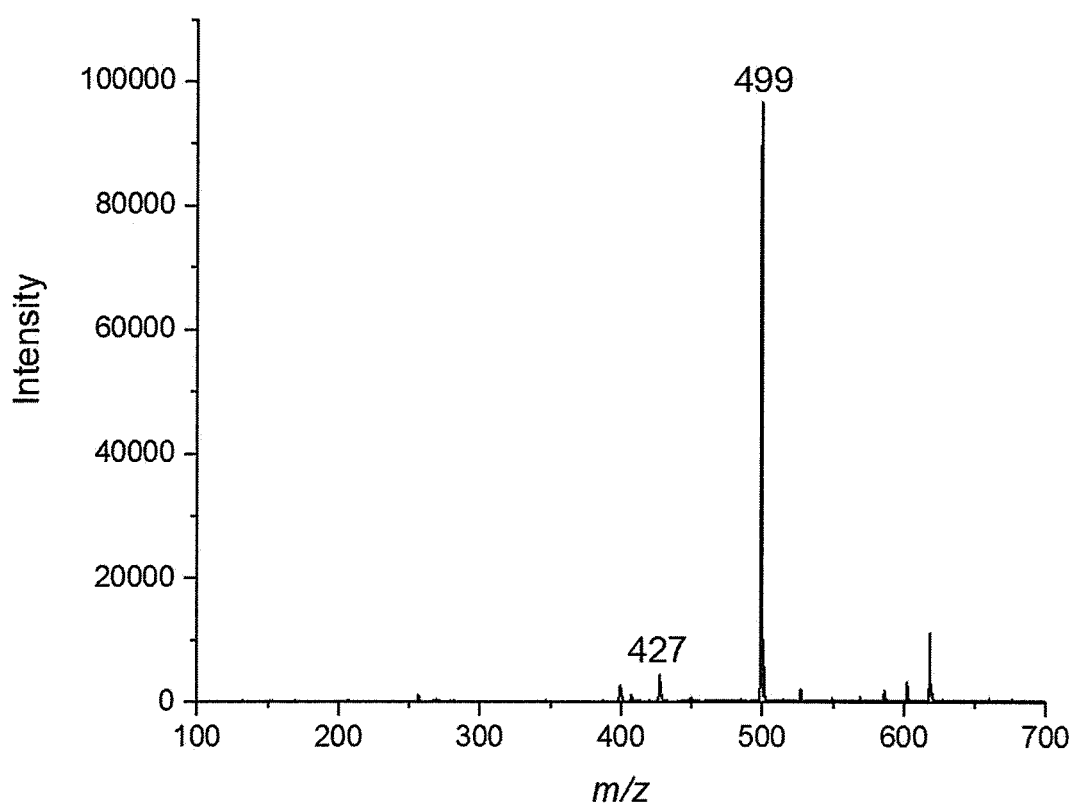
FIG. 5 is a full scan mass spectrum of the mass to charge ratio (X-axis, labeled "m/z") vs. the intensity (Y-axis, labeled "intensity") for a soil sample examined using the sample collection device described herein.

A soil sample was collected using the sample collection device of Example 1 from soil around a legacy Navy AFFF test facility. No sample pre-treatment was performed and the contaminated soil was collected into the sample collection device for analysis. The results are shown in FIG. 5. The full scan shows the presence of fluorotelomer sulfonic acid 6:2 (6:2 FtS) (m/z 427) and perfluorooctanesulfonic acid (PFOS) (m/z 499), which were identified by their $[M-H]^-$ ion.

As used herein, the term "about" is used to provide flexibility to a numerical range endpoint by providing that a given value may be "a little above" or "a little below" the endpoint. The degree of flexibility of this term can be dictated by the particular variable and would be within the knowledge of those skilled in the art to determine based on experience and the associated description herein.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Unless otherwise stated, any feature described herein can be combined with any aspect or any other feature described herein.

Reference throughout the specification to "one example", "another example", "an example", and so forth, means that a particular element (e.g., feature, structure, and/or characteristic) described in connection with the example is included in at least one example described herein, and may or may not be present in other examples. In addition, it is to be understood that the described elements for any example may be combined in any suitable manner in the various examples unless the context clearly dictates otherwise.

It is to be understood that the ranges provided herein include the stated range and any value or sub-range within the stated range. For example, a range from about 0.15 mm to about 0.25 mm should be interpreted to include not only the explicitly recited limits of from about 0.15 mm to about 0.25 mm, but also to include individual values, such as 0.18 mm, 0.20 mm, 0.21 mm, etc., and sub-ranges, such as from about 0.17 mm to about 0.20 mm, etc.

In describing and claiming the examples disclosed herein, the singular forms "a", "an", and "the" include plural referents unless the context clearly dictates otherwise.

What is claimed is:

1. A sample collection device, comprising:
   a sample collection cone comprised of conductive polymer, wherein the conductive polymer includes a mixture of carbon nanotubes and a polymer; and
   wherein the sample collection cone has a hole having a diameter configured to retain sample media within the sample collection cone and allow solvent extraction after a solvent passes through the sample media within the sample collection cones;
   wherein the hole diameter having a size ranging from 0.15 mm to 0.25 mm.

2. The sample collection device of claim 1, wherein the sample collection cone is a multifaced pyramid or a cylindrical cone.

3. The sample collection device of claim 1, wherein the sample collection device has a width that is large enough to hold a solid media sample, but small enough to remain portable while using the least amount of material as possible ranging from 12.5 mm to 40 mm.

4. The sample collection device of claim 1, wherein the sample collection device has a height that is large enough to hold a solid media sample, but small enough to remain portable while using the least amount of material as possible ranging from 12.5 mm to 40 mm.

5. The sample collection device of claim 1, wherein the sample collection device has a thickness large enough to hold a solid media sample, but small enough to retain the device's original shape while using the least amount of material as possible ranging from 0.6 mm to 3 mm.

6. The sample collection device of claim 1, wherein the carbon nanotubes are multi-wall carbon nanotubes.

7. The sample collection device of claim 1, wherein the polymer is selected from the group consisting of polyethylene terephthalate, acrylonitrile butadiene styrene, polylactic acid, polyetherketoneketone, polyether ether ketone, polycarbonate, polyphenylene sulfide, polyvinylidene fluoride, and combinations thereof.

8. A method for testing solid media composition, comprising:
   preparing the sample collection device of claim 1;
   filling the sample collections device of claim 1 with solid media containing an analyte;
   applying a solvent to the solid media and applying a voltage to the sample collection device; and
   performing a sample analysis, thereby determining an analyte composition, analyte concentration, or analyte presence within the solid media.

9. The method of claim 8, wherein the voltage ranges from about 4 kV to about 7 kV.

10. The method of claim 8, wherein the analyte includes a contaminant selected from the group consisting of perfluoroalkyl substances, polyfluoroalkyl substances, energetics, chemical warfare agent simulants, drugs of abuse, and combinations thereof.

11. The method of claim 8, wherein the solid media is selected from the group consisting of soil, sand, sediment, waste, pure analytes, and combinations thereof.

12. The method of claim 8, wherein the sample collection cone is a multifaced pyramid or a cylindrical cone.

13. The method of claim 8, wherein the sample collection device has a width that is large enough to hold a solid media sample, but small enough to remain portable while using the least amount of material as possible ranging from 12.5 mm to 40 mm.

14. The method of claim 8, wherein the sample collection device has a height that is large enough to hold a solid media sample, but small enough to remain portable while using the least amount of material as possible ranging from 12.5 mm to 40 mm.

15. The method of claim 8, wherein the sample collection device has a thickness large enough to hold a solid media sample, but small enough to retain the device's original shape while using the least amount of material as possible ranging from 0:6 mm to 3 mm.

16. The method of claim 8, wherein the carbon nanotubes are multi-wall carbon nanotubes.

17. The method of claim 8, wherein the polymer is selected from the group consisting of polyethylene terephthalate, acrylonitrile butadiene styrene, polylactic acid, polyetherketoneketone, polyether ether ketone, polycarbonate, polyphenylene sulfide; polyvinylidene fluoride, and combinations thereof.

18. The method of claim 8, wherein the sample analysis is performed using a Mass spectrometer or an ion mobility spectrometer.

19. The method of claim 8, wherein the solvent is selected from the group consisting of methanol, ethanol, propanol, isopropanol, acetonitrile, water, water mixed with organic solvents, and combinations thereof.

20. The method of claim 19, wherein the solvent further includes additives selected from the group consisting of acetic acid, formic acid, ammonium acetate, and combinations thereof.

* * * * *